United States Patent
Zappala

[19]

[11] Patent Number: 6,117,133
[45] Date of Patent: Sep. 12, 2000

[54] MULTIPLE-LUMEN SHEATH FOR A RESECTOSCOPE

[76] Inventor: Stephen M. Zappala, 98 Rattlesnake Hill Rd., Andover, Mass. 01810

[21] Appl. No.: 09/277,536

[22] Filed: Mar. 26, 1999

Related U.S. Application Data

[60] Provisional application No. 60/080,661, Apr. 3, 1998.

[51] Int. Cl.[7] .................................................. A61B 17/36
[52] U.S. Cl. ................................................ 606/46; 606/41
[58] Field of Search ......................................... 606/41–50

[56] References Cited

U.S. PATENT DOCUMENTS

| | | | |
|---|---|---|---|
| 4,116,198 | 9/1978 | Roos ............................................. | 606/46 |
| 5,697,882 | 12/1997 | Eggers et al. ............................... | 604/114 |
| 5,860,951 | 1/1999 | Eggers et al. ............................... | 604/22 |
| 5,885,277 | 3/1999 | Korth ........................................... | 606/35 |
| 5,902,272 | 5/1999 | Eggers et al. ............................... | 604/114 |
| 5,916,215 | 6/1999 | Long et al. .................................. | 606/41 |
| 5,925,044 | 7/1999 | Hofmann et al. ........................... | 606/46 |
| 6,045,532 | 4/2000 | Eggers et al. ............................... | 604/114 |
| 6,047,700 | 4/2000 | Eggers et al. ............................... | 128/898 |

*Primary Examiner*—Linda C. M. Dvorak
*Assistant Examiner*—David M. Ruddy
*Attorney, Agent, or Firm*—Nields, Lemack & Dingman; Brian M. Dingman

[57] ABSTRACT

A multiple-lumen sheath which fits over a resectoscope and provides an electrosurgical resection energy (radio frequency) return path and at least one irrigant channel, comprising, a sheath body which fits over the resectoscope; a conductor disposed within the sheath body for carrying the electrosurgical resection energy; and an irrigant channel within the sheath body and outside of the conductor, for both carrying irrigant fluid and cooling the conductor.

7 Claims, 3 Drawing Sheets

MULTIPLE-LUMEN SHEATH FOR A RESECTOSCOPE

CROSS-REFERENCE

This is a continuation-in-part of U.S. application Ser. No. 60/080,661 filed on Apr. 3, 1998.

FIELD OF THE INVENTION

This invention relates to a sheath for resectoscopes and more specifically to a resectoscope sheath which provides bipolar capabilities without the risk of thermal injury.

BACKGROUND OF THE INVENTION

Transurethral resection of the prostate (TURP) is the primary modality to alleviate bladder outflow obstruction secondary to benign enlargement of the prostate gland. However, this procedure has several potential complications including life threatening dilutional hyponatremia from the absorption of hypotonic irrigating media such as water, glycine or sorbitol. The absorptive hyponatremia is attributed to several surgical occurrences including perforation of the prostatic capsule, fenestration of a vascular sinus or a prolonged resection time.

On the other hand, utilization of the preferred irrigating media, physiologic 0.9 N saline, for an endoscopic resection using a standard monopolar energy source is not feasible because a substantial portion of the radiofrequency energy source to the resectoscope (from a electrosurgical generator) is dissipated within the ionic nature of the sodium chloride. Thus, use of monopolar energy has fallen out of favor with most endoscopic surgeons, whether they are attempting to perform urologic, gynecologic, arthroscopic or laparoscopic resections.

Sleeves for resectoscopes, which accommodate a bipolar energy source and which deliver the electrosurgical radiofrequency within a saline medium, are known in the art. However, the outer protective coating of these sleeves of these bipolar devices abuts the urethra. Although the outer protective coating of the sleeve potentially protects the urethra from the return electrode, any interruption in the continuous irrigation flow apparatus, whether inflow or outflow, causes a devastating thermal injury throughout the entire length of the male urethra. This type of injury requires extensive reconstructive surgery, urinary incontinence, sexual dysfunction or a combination thereof.

SUMMARY OF THE INVENTION

It is therefore a primary object of this invention to provide a resectoscope sheath which provides bipolar capabilities without the risk of thermal injury.

It is a further object of this invention to provide a resectoscope sheath which enables a physician to use a physiological saline solution as the irrigant without the problem of dissipating electrosurgical energy.

It is a further object of this invention to provide a resectoscope sheath which is disposable and which increases the margin of safety for a bipolar resection using saline as the irrigating medium.

It is a further object of this invention to provide a resectoscope sheath in which the coaxial cable is not in direct contact with the patient's urethra.

It is a further object of this invention to provide a resectoscope sheath in which the outflowing irrigant is used to cool the coaxial cable of a bipolar resecting device.

It is a further object of this invention to provide a resectoscope sheath which enables a urologist to perform a prostatectomy under direct vision and tissue ablation rather than dessication (vaporization).

It is a further object of this invention to provide a resectoscope sheath which does not require extensive start up costs or a steep learning curve.

It is a further object of this invention to provide a bipolar resectoscope sheath which permits standard electrosurgical current with saline as the irrigant rather than a hypotonic solution and which slides easily over a continuous flow resectoscope.

It is a further object of this invention to provide a bipolar resectoscope sheath which protects against urethral injuries and stricture disease without altering the efficacy of the sheath.

It is a further object of this invention to provide a resectoscope sheath which enables the resectionist to concomitantly coagulate and debulk in a relatively clear operating environment without having to see through the pink hue caused by lysed erythrocytes associated with hypotonic solutions such as water or sorbitol.

It is a further object of this invention to provide a resectoscope sheath which does not require the resectionist to adhere to a "1 gm/1 minute" guideline of a sixty minute resection time to avoid dilutional hyponatremia.

A preferred embodiment of the multiple-lumen sheath of this invention which fits over a resectoscope and provides an electrosurgical resection energy (radio frequency) return path and at least one irrigant channel, comprises: a sheath body which fits over the resectoscope; a conductor disposed within the sheath body for carrying the electrosurgical resection energy; and an irrigant channel within the sheath body and outside of the conductor, for both carrying irrigant fluid and cooling the conductor. The sheath body preferably comprises a second irrigant channel within the sheath body, for carrying irrigant fluid in the opposite direction to the fluid flow in the first irrigant channel. The sheath body has a proximal end and a distal end and may further comprise an external suction opening in the sheath body proximate the distal end which leads into the irrigant channel.

The sheath body may also comprise three concentric lumens about a hollow center adapted to receive the resectoscope therein, wherein the three concentric lumens comprise an outer lumen, an intermediate lumen and a inner lumen. The outer lumen may carry irrigant flowing outward from an area of resection, the intermediate lumen may carry the conductor, and the inner lumen may carry irrigant flowing inward toward the area of resection.

The sheath body also preferably comprises a locking device proximate the proximal end for securely holding the resectoscope within the sheath body, and the conductor preferably is a coaxial cable capable of carrying the electrosurgical resection energy to and from a resection area. In addition, the sheath body may be made of stainless steel or a hydrophilic coated sialastic material.

Another preferred embodiment of the multiple-lumen sheath of the invention which fits over a resectoscope and provides an electrosurgical resection energy (radio frequency) return path and at least one irrigant channel, comprises: a sheath body which fits over the resectoscope, wherein the sheath body comprises three concentric lumens about a hollow center adapted to receive the resectoscope therein; a conductor disposed within the sheath body for carrying the electrosurgical resection energy; an irrigant channel within the sheath body and outside of the conductor, for both carrying irrigant fluid and cooling the conductor. Similar to the above first described embodiment, the sheath body preferably comprises three concentric lumens comprise an outer lumen, an intermediate lumen and a inner lumen, wherein the outer lumen carries irrigant flowing outward from an area of resection and the intermediate lumen carries the conductor.

Yet another preferred embodiment of the multiple-lumen sheath of the invention which fits over a resectoscope and provides an electrosurgical resection energy (radio frequency) return path and at least one irrigant channel, comprises: a sheath body which fits over the resectoscope, wherein the sheath comprises three concentric lumens comprising an outer lumen, an intermediate lumen and a inner lumen; a conductor disposed within the intermediate lumen, the conductor is a coaxial cable capable of carrying the electrosurgical resection energy to and from a resection area; and an irrigant channel within the sheath body and outside of the conductor, for both carrying irrigant fluid and cooling the conductor.

The invention may be adapted to fit virtually any size resectoscope used to perform urologic, gynecologic, arthroscopic or laparoscopic resections.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS

The multiple-lumen sheath of the invention which fits over a resectoscope generally comprises, a sheath body which fits over the resectoscope, a conductor disposed within the sheath body for carrying the electrosurgical resection energy, and an irrigant channel, within the sheath body and outside of the conductor, for carrying both the irrigant fluid and cooling the conductor. The sheath body is made up of a hollow central core surrounded by three generally concentric lumens in which the outer and inner lumens carry the irrigant out of and into the resection area and the intermediate lumen carries the conductor. The hollow core is adapted to receive at least a portion of a resectoscope therein.

Figure 1:
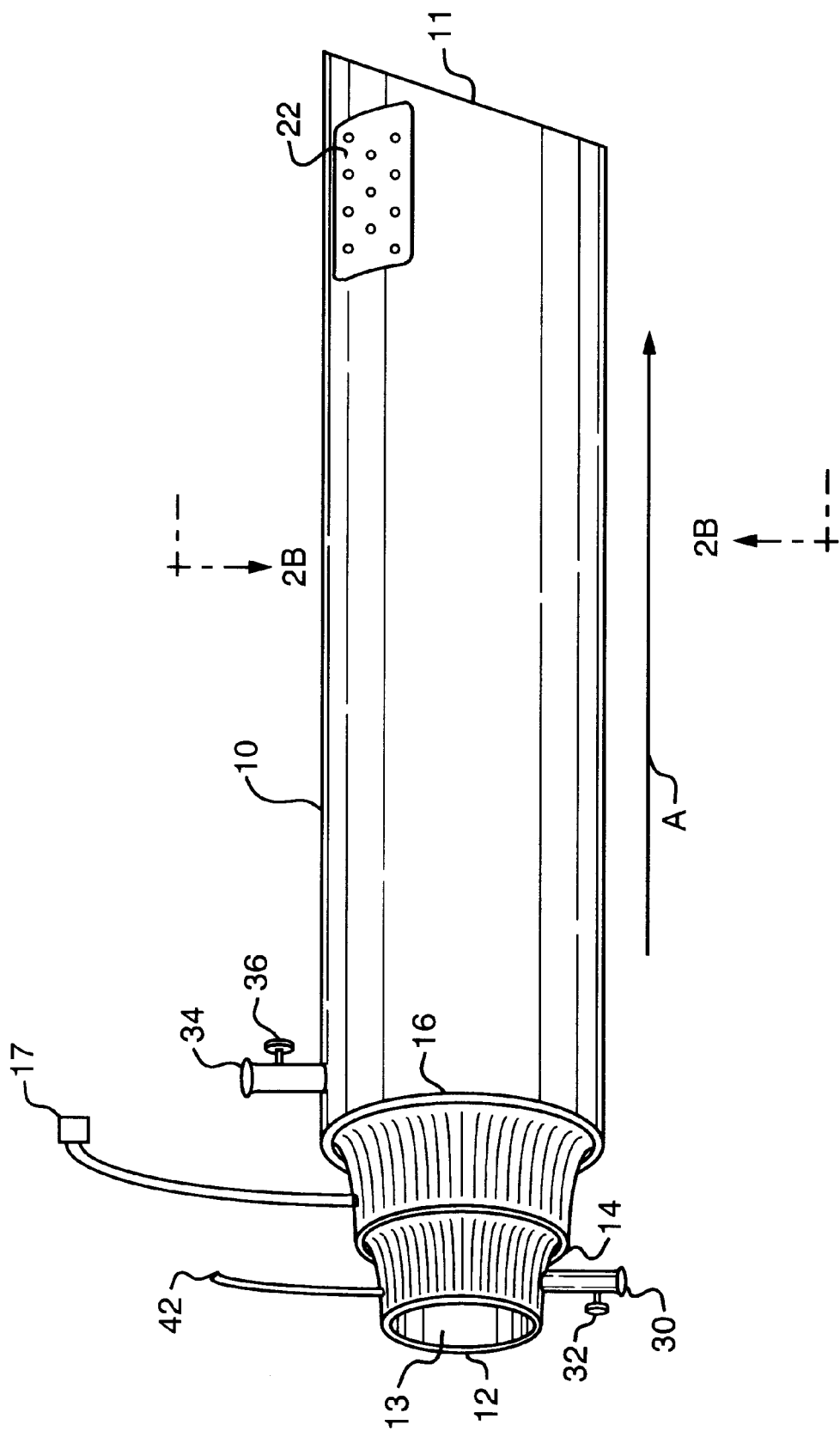
FIG. 1 is an enlarged, schematic side view of the preferred embodiment of the multiple-lumen sheath of this invention.

FIG. 1 illustrates a preferred embodiment of the multiple-lumen sheath, generally referred to as sheath 10, of the invention for use with a resectoscope. Sheath 10 is preferably a triple lumen sheath made of stainless steel or a hydrophilic coated sialastic which defines a central hollow core 18 into which a standard resectoscope would fit. Resectoscopes are readily available from companies such as Storz, Olympus, Wolf and ACMI. The sheath of the invention is designed to engage any of these resectoscopes in a manner which would be understood by someone of ordinary skill in the art using a locking mechanism such as locking mechanism 42 (FIG. 1).

Figure 2A:
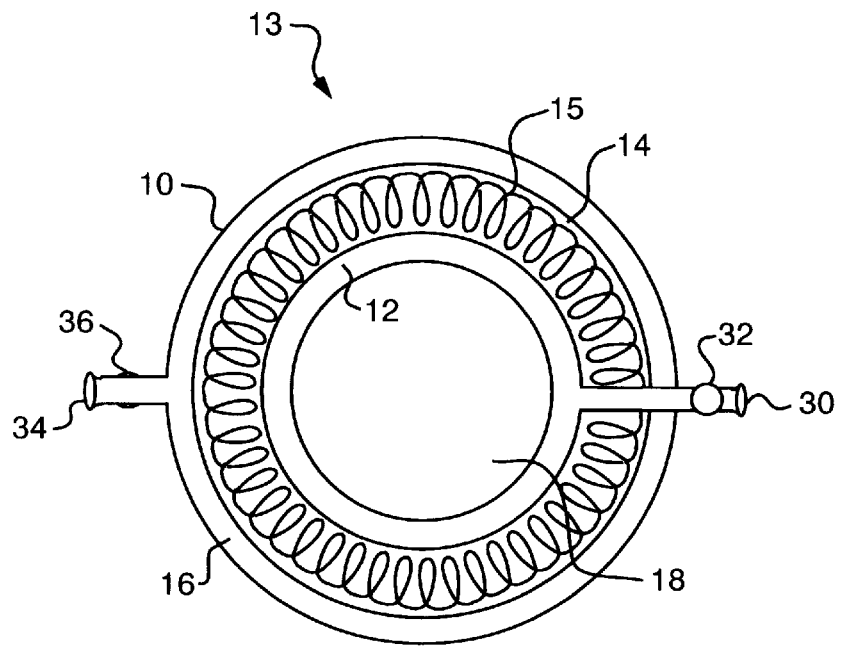
FIG. 2A is an end view depicting the physician end (proximal end) of the sheath of FIG. 1.
Figure 2B:
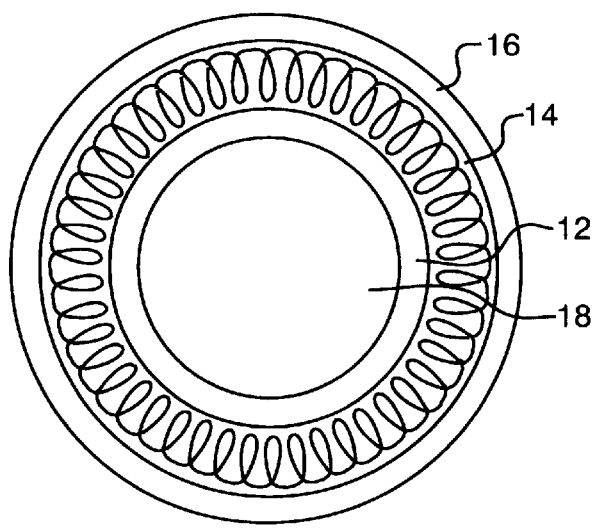
FIG. 2B is a cross-sectional view taken at about the midsection of the sheath of FIG. 1.
Figure 3:
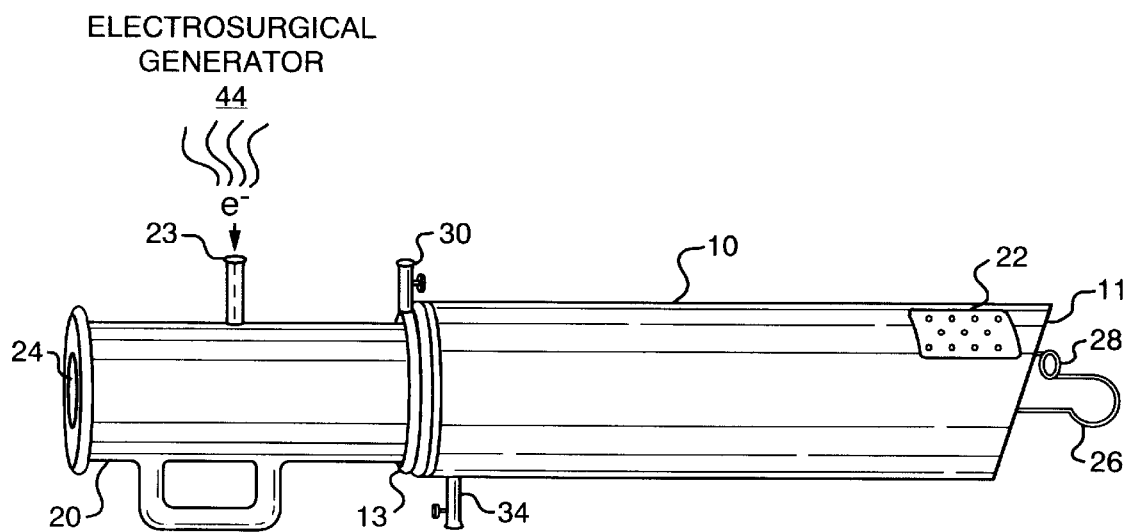
FIG. 3 is a schematic view of the sheath in place over a standard resectoscope.

As shown in FIGS. 1 and 2A, sheath 10 defines an inner tapered tubular space 18 which can accept a standard resectoscope. The diameter of sheath 10 tapers down from proximal end 13 (physician end) to distal end 11 (resection area end) in the direction of arrow A. Sheath 10 also defines three concentric annular lumina 12, 14 and 16. Intermediate lumen 14 carries electrical conductor 15 which acts as the return path for the electrosurgical resection energy which has been supplied to resectoscope loop 26 of resectoscope 10, FIG. 3. Inner lumen 12 and outer lumen 16 preferably carry a physiologic saline irrigant, although a standard irrigant such as glycine, sorbitol or water can be used, to and from, respectively, the area being resected. Suction return port 22 is located proximate distal end 11 on the outside surface of sheath 10. Resectoscope 20 typically includes an ocular lens 24 at the proximal end of resectoscope 20, a resection area lens 28 proximate the distal end of resectoscope 20 and electrical connector 23 for receiving the electrosurgical resection energy from electrosurgical generator 44, (ESU), schematically shown in FIG. 3.

Inner lumen 12 is provided with the irrigant inflow through inlet tube 30 and control valve 32. Outer lumen 16, in such instance, is preferably used to carry the irrigant suction or outflow, through tube 34 and valve 36. Any resistive heating of conductor 15 is dissipated by the irrigant flowing through outer lumen 16, thus protecting the urethra from thermal damage, because irrigant flowing through annular lumen 16 completely surrounds the conductor. Conductor 15 is preferably a coaxial cable provided with external cord 17 for connecting conductor 15 with ESU 44. Sheath 10, together with the coaxial cable, enables a physician to utilize a physiologic saline solution as the irrigant, instead of water, glycine or sorbitol, because the internal coaxial cable acts as a return electrode which allows ESU 44 to act as a bipolar energy source. This design solves the problem of energy dissipation associated with an ionic saline irrigant when used in connection with a monopolar energy source and a standard ground dispersion pad.

Figure 2C:
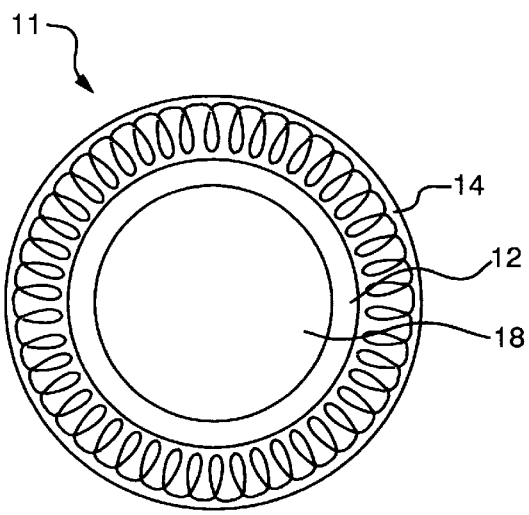
FIG. 2C is an end view of the patient bladder end (distal end) of the sheath of FIG. 1.

Distal end 11, shown in FIG. 2C, does not show annular lumen 16 because suction return port 22 opens to the outside surface of sheath 10 and leads directly into annular lumen 16. This arrangement provides an irrigant pickup close to distal end 11 of sheath 10 near resectoscope loop 26, but not directly adjacent to the irrigant inflow from inner lumen 12, which prevents the inflowing irrigant from being channeled directly back into the suction return lumen without first having flowed into and around the tissue area to be resected.

To use the sheath of the invention, sheath 10 may be installed over a #26 Fr Storz resectoscope (Karl Storz Endoscopy—America, Culver City, Calif.) with a standard 0.014 resectoscope loop electrode. A Force II electrosurgical generator from Valley Lab, Boulder, Colo. may be used, setting the monopolar energy at 200 watts, pure cut, with 75 watts, coagulation. The bipolar sheath creates a total external diameter of 28.5 Fr, thus a urethral dilation to 30 Fr with van Buren sounds facilitates the sleeve insertion. An optical video system in conjunction with continuous flow is used. Normal saline and a fluid warmer delivers the irrigant at a height approximately 60 cm above the operative field. Only minor variations from a standard electrosurgical resection of the prostate are required.

The sheath of the invention functions to disperse the monopolar oscillating radio frequency wave from the ESU. The current path travels from the active loop electrode, through the prostatic tissue and also through the saline, subsequently traversing the bipolar sleeve and returning to the ESU. The bipolar sleeve thus may be interpreted as a return electrode. Thus, a dispersive ground pad is not necessary since the current path travels through the sleeve and the ionic effects of the saline irrigant are minimized. It is imperative that the tissue to be resected be interposed between the resectoscope loop and the bipolar sleeve in order to optimize the cutting efficacy. The anterior urethra is insulated from the conductive component of the sleeve by its outer insulation. Use of the sheath of the invention does not mandate any selection parameters on the resectionist based upon anatomy such as the presence of a median lobe, total prostatic volume or lobe asymmetry. The sheath may be used using direct vision and does not require ancillary imaging systems.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A multiple-lumen sheath which fits over a resectoscope and provides an eletrosurgical resection energy (radio frequency) return path and at least one irrigant channel, comprising,
   a sheath body, which fits over said resectoscope, comprising
   an outer lumen, wherein said outer lumen carries irrigant flowing outward from an area of resection;
   an intermediate lumen, wherein said intermediate lumen carries a conductor for said electrosurgical resection energy; and
   an inner lumen, wherein said inner lumen carries irrigant flowing inward toward said area of resection.

2. The multiple-lumen sheath of claim 1, wherein said sheath body has a proximal end and a distal end, further comprising an external suction opening in said sheath body proximate said distal end which leads into said irrigant channel.

3. The multiple-lumen sheath of claim 1, wherein said sheath body comprises three concentric lumens about a hollow center adapted to receive said resectoscope therein.

4. The multiple-lumen sheath of claim 1, wherein said sheath body has a proximal end and a distal end, further comprising a locking device proximate said proximal end for securely holding said resectoscope within said sheath body.

5. The multiple-lumen sheath of claim 1, wherein said conductor is a coaxial cable capable of carrying said electrosurgical resection energy to and from a resection area.

6. The multiple-lumen sheath of claim 1, wherein said sheath body is made of a hydrophilic coated sialastic material.

7. A multiple-lumen sheath which fits over a resectoscope and provides an eletrosurgical resection energy (radio frequency) return path and at least one irrigant channel, comprising,
   a sheath body, which fits over said resectoscope, wherein said sheath body comprises three concentric lumens about a hollow center adapted to receive said resectoscope therein, comprising, an outer lumen, wherein said outer lumen carries irrigant flowing outward from an area of resection;
   an intermediate lumen, wherein said intermediate lumen carries a conductor for said electrosurgical resection energy, and wherein said conductor is a coaxial cable capable of carrying said electrosurgical resection energy to and from said resection area; and
   an inner lumen, wherein said inner lumen carries irrigant flowing inward toward said resection area.

* * * * *